US006764482B2

(12) United States Patent
Keilman et al.

(10) Patent No.: US 6,764,482 B2
(45) Date of Patent: *Jul. 20, 2004

(54) DUAL-FILLED TWIN BAG, A PACKAGE AND A METHOD FOR FORMING A PACKAGE FOR ADMINISTERING A SOLUTION

(75) Inventors: Michael R. Keilman, McHenry, IL (US); Walter A. Makaryk, Mt. Prospect, IL (US); Joseph A. Giertych, Lake Forest, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/283,654

(22) Filed: Oct. 29, 2002

(65) Prior Publication Data

US 2003/0114788 A1 Jun. 19, 2003

Related U.S. Application Data

(63) Continuation of application No. 09/349,688, filed on Jul. 8, 1999, now Pat. No. 6,508,800, which is a division of application No. 08/755,940, filed on Nov. 25, 1996, now abandoned, which is a continuation-in-part of application No. 08/646,647, filed on May 3, 1996, now Pat. No. 5,820,582.

(51) Int. Cl.$^7$ .......................... A61B 19/00; A61M 1/00; B65D 73/00; B65D 75/00

(52) U.S. Cl. .................. 604/410; 604/29; 604/408; 206/466; 206/469; 206/828; 128/DIG. 24; 436/18

(58) Field of Search .................. 604/4.01, 5.01–5.04, 604/28–30, 49, 80, 82, 257, 259, 262, 403, 408, 410, 416, 615; 206/438, 466, 469, 828; 128/DIG. 24; 436/18, 163; 383/37, 105, 109, 127, 904; 53/396, 425, 431, 449, 452, 457, 459, 467, 469, 476, 473–74, 266.1; 422/600, 682, 686, 717; 514/832, 833; 222/92–96, 1, 105, 129–30, 133, 143, 145.1, 206–7, 215, 630, 372, 394; 210/645–47, 96.1, 101, 257.1, 542, 321.71–321.72; 137/88, 89

(56) References Cited

U.S. PATENT DOCUMENTS 3,110,308 A    11/1963   Bellamy, Jr.
3,945,380 A     3/1976   Dabney et al.
4,306,976 A    12/1981   Bazzato (List continued on next page.)

FOREIGN PATENT DOCUMENTS

DE        42 13 681       11/1993
DE        44 10 875 A1    10/1995
DE        44 10 876 A1    10/1995

(List continued on next page.)

OTHER PUBLICATIONS

"Aseptic Exchange Procedure," brochure published by Baxter Healthcare Corporation, McGaw Park, IL 1992.
Balteau, Patrick R. et al. "Design and Testing of the Baxter Integrated Disconnect System," in *Peritoneal Dialysis International*, vol. 11, pp. 131–136, 1991.
"The Next Step in the Evolution of CAPD," brochure published by Baxter Healthcare Corporation, McGaw Park, IL 1993.

(List continued on next page.)

*Primary Examiner*—Patricia Bianco
(74) *Attorney, Agent, or Firm*—Paula J. F. Kelly; Joseph P. Reagen; Bell, Boyd & Lloyd LLC

(57) ABSTRACT

A dual-filled twin bag, a packaging including the twin bag, and a method for forming the packaged twin bags are provided. Each of two bags, a solution bag (10) and a drain bag (12) for a system used for a peritoneal dialysis procedure, are filled, at least partially, with a solution (14). A tubing set (16) connects the two filled bags (10,12) and may also be filled with solution (14) which is added to the bags (10,12) and the tubing set (16) during the manufacturing process. Alternatively, the tubing set (16) may be filled with air. The tubing set (16) is sandwiched between the solution bag (10) and the drain bag (12) and subsequently packaged in an overpouch (24). The method for forming the package including the bags filled with solution is simplified and the overall package size is reduced due to the sandwiched tubing set (16) between the solution bags (10,12) and the provision of solution in both bags (10,12).

9 Claims, 2 Drawing Sheets

U.S. PATENT DOCUMENTS

| | | | |
|---|---|---|---|
| 4,326,526 A | * 4/1982 | Buck et al. | 604/29 |
| 4,548,605 A | * 10/1985 | Iwamoto et al. | 604/410 |
| 4,610,670 A | 9/1986 | Spencer | |
| 4,657,540 A | 4/1987 | Iwamoto et al. | |
| 5,336,173 A | 8/1994 | Folden | |
| 5,338,293 A | 8/1994 | Jeppsson et al. | |
| 5,560,403 A | 10/1996 | Balteau et al. | |
| 5,601,730 A | 2/1997 | Page et al. | |
| 5,836,934 A | 11/1998 | Beshel | |
| 5,879,318 A | 3/1999 | Van Der Heiden et al. | |
| 6,012,578 A | * 1/2000 | Keilman | 206/438 |
| 6,060,138 A | 5/2000 | Carmen et al. | |
| 6,348,049 B1 | * 2/2002 | Spencer | 604/523 |
| 6,508,800 B1 | * 1/2003 | Keilman et al. | 604/410 |

FOREIGN PATENT DOCUMENTS

| | | |
|---|---|---|
| WO | WO 83/02061 | 6/1983 |
| WO | WO 88/06895 | 9/1988 |
| WO | WO 94/25084 | 11/1994 |
| WO | WO 95/08299 | 3/1995 |

OTHER PUBLICATIONS

"Twin Bag Procedure Guide," brochure published by Baxter Healthcare Corporation, McGaw Park, IL 1993.

"Twin Bag Spectrum 1:30—Setting New Standard in CAPD Systems," Brochure published by Baxter Healthcare Corporation, McGaw Park, IL 1994.

* cited by examiner

DUAL-FILLED TWIN BAG, A PACKAGE AND A METHOD FOR FORMING A PACKAGE FOR ADMINISTERING A SOLUTION

This application is a continuation of U.S. patent application Ser. No. 09/349,688, filed on Jul. 8, 1999, now U.S. Pat. No. 6,508,800, which is a divisional of U.S. patent application Ser. No. 08/755,940, filed on Nov. 25, 1996, now abandoned, which is a continuation-in-part application of U.S. patent application Ser. No. 08/646,647 filed on May 3, 1996, now U.S. Pat. No. 5,820,582.

BACKGROUND OF THE INVENTION

The present invention generally relates to a dual-filled twin bag system, a package and a method for forming a package. More specifically, the present invention relates to a dual-filled twin bag including dialysis solution in each bag wherein the twin bag is used for administering dialysis solution to a patient undergoing peritoneal dialysis.

It is, of course, generally known to store a dialysis solution in a flexible plastic bag for use in continuous ambulatory peritoneal dialysis (CAPD). The dialysis solution is transferred from the bag to a patient during a dialysis procedure. A second empty bag is provided for draining liquid from a peritoneal cavity of an individual undergoing peritoneal dialysis. In conventional twin bag systems, the empty bag and bag containing solution are interconnected by a set of tubing that attaches to a tubing set that ultimately connects to the patient catheter.

A solution bag, the bag containing the dialysis solution, is generally completely filled and ready for use after a sterilization procedure is performed. The sterilization procedure requires that the bag is oriented on a sterilizing tray or other device to sterilize the solution contained in the bag. Due to the volume of solution in the bag, sterilization is a time-consuming process. That is, due to the volume of solution creating a wide profile of the solution in the bag, heat penetration to effect complete sterilization of the solution, the bag and the tubing set is time-consuming.

To transport a solution bag, a drain bag, and a tubing set to a patient, the combination is placed in an overpouch. The overpouch is designed in order to accommodate the three components. However, it is often difficult and cumbersome to place the three components in an overpouch, particularly when the method is performed automatically. Namely, the tubing set often is tangled with the overpouch or the drain bag during placement into the overpouch. Furthermore, due to the profile obtained by filling a single solution bag, the overall profile of a conventional twin bag product within an overpouch tends to be bulky. This overall bulkiness of a conventional twin bag product itself further requires a correspondingly large shipping carton. Additionally, substantial storage space is required in the home or place at which an individual undergoes peritoneal dialysis. The amount of packaging also generates substantial trash to completely dispose of the product, including the packaging of the product, following use.

At the start of a typical cycle of CAPD, solution is drained from the peritoneal cavity into the drain bag through one line of the tubing set. After draining, a frangible in another line of the tubing set from the solution bag is broken to allow fluid communication between solution in the solution bag to be fed to the peritoneal cavity. Often, for physically or visually impaired patients, the frangibles are difficult to break. In addition, particulate matter from the breaking of the frangible may obstruct the fluid path. Moreover, use of a frangible in a tubing set may cause fibrin clots at the ends of the broken frangible parts.

A need, therefore, exists for an improved solution container and associated tubing set, particularly for use during a peritoneal dialysis procedure, which overcomes the deficiencies known in other systems that use a solution bag and a drain bag for administering a solution to a patient and subsequently drain the solution to a container.

SUMMARY OF THE INVENTION

The present invention relates to a dual-filled twin bag, a package including the bag and a method for forming a package for administering a solution. More specifically, the present invention relates to a twin-bag package, particularly useful for administering a solution used in a peritoneal dialysis procedure. The package is formed in such a manner to substantially reduce packaging size requirements and to simplify the packaging procedure.

To this end, the present invention provides a system having a solution bag with an interior holding a dialysis solution and a drain bag having an interior holding a dialysis solution. A tubing set including a length of tubing connects the solution bag and the drain bag.

In an embodiment, the dialysis solution in the solution bag is identical to the dialysis solution in the drain bag.

In an embodiment, the tubing set includes a coiled length of tubing.

In an embodiment, the solution bag and the drain bag are constructed of flexible plastic material.

In an embodiment, the tubing set includes a dialysis solution within the tubing set.

In an embodiment, the system has a first length of coiled tubing and a second length of coiled tubing wherein the first length and the second length are attached to form a multiple ring coil.

In an embodiment, a connector is attached to an end of the tubing set.

In an embodiment, a cap encloses an end of the connector attached to the end of the tubing set. The aforementioned cap may be steam permeable.

In an embodiment, the solution bag and the drain bag are partially filled with the dialysis solution.

In an embodiment, the volumes of the dialysis solution in the solution bag and the drain bag are substantially equal.

In an embodiment, the tubing set is filled with a gas.

In another embodiment of the present invention, a packaged system is provided. The packaged system has a first container having exterior walls defining an interior wherein the interior includes a first solution. A second container having exterior walls defines an interior wherein the interior includes a second solution. A tubing set is sandwiched between one of the exterior walls of the first container and one of the exterior walls of the second container wherein the tubing set connects the first container to the second container.

In an embodiment, the exterior walls of the first container and the second container sandwiching the tubing set are arranged such that the exterior walls are substantially flush with respect to each other.

In an embodiment, a third container has an interior constructed and arranged to completely encompass the first container, the second container and the tubing set.

In an embodiment, the tubing set includes a solution therein.

In an embodiment, the tubing set includes a coiled length of tubing.

In an embodiment, the first container and the second container are constructed from flexible materials.

In an embodiment, the first solution of the first container is identical to the second solution of the second container.

In an embodiment, the solution of the first container is a dialysis solution.

In an embodiment, the first and second solutions are added to the first container and the second container during manufacture of the first container and the second container.

In an embodiment, the first container is a solution bag used during a dialysis procedure.

In an embodiment, the second container is a drain bag for use during a dialysis procedure.

In another embodiment of the present invention, a method is provided for forming a package for use during a peritoneal dialysis procedure. The method comprises the steps of: providing a first container defining an interior; providing a second container defining an interior; connecting the first container and the second container; and filling simultaneously and at least partially the interiors of the first container and the second container with a solution.

In an embodiment, a tubing set is provided including a length of tubing to connect the first container and the second container.

In an embodiment, a third container defining an interior is provided. The first container and the second container are placed in the interior of the third container.

In an embodiment, the tubing set is sandwiched between an exterior wall of the first container and an exterior wall of the second container.

In an embodiment, the first container and the second container include substantially equal amounts of the solution.

In an embodiment, a coiled length of tubing is provided to connect the first container and the second container.

In another embodiment, the first container and the second container are constructed from flexible materials.

In an embodiment, the solution in the first container is a different solution from the solution in the second container.

In an embodiment, the tubing set is filled with a gas.

In another embodiment of the present invention, a method is provided for administering a solution to a patient. The method comprises the steps of: providing a first bag having a portion of the solution therein; providing a second bag having another portion of the solution therein; connecting the first bag and the second bag to provide fluid communication therebetween; transferring the portion of the solution in the first bag to the second bag; and feeding the solution in the second bag to the patient.

In an embodiment, flow of solution into the first bag following transfer to the second bag is prevented.

In an embodiment, the transferring and the feeding are performed without using a frangible.

In an embodiment, the volumes of solutions in the first bag and the second bag are substantially equal.

In an embodiment, the solution is a dialysis solution.

In an embodiment, the solution in the first bag is a different solution than a solution in the second bag.

In an embodiment, the tube connecting the first bag to the second bag is filled with a gas.

It is, therefore, an advantage of the present invention to provide a system, a package and a method for packaging that includes dialysis solution in both a solution bag and a drain bag.

Another advantage of the present invention is to provide a system, a package and a method for performing peritoneal dialysis that does not require the use of frangibles.

Yet another advantage of the present invention is to provide a system, a package and a method for peritoneal dialysis that reduces the overall size and profile of the package.

And, another advantage of the present invention is to provide a system, a package and a method that simplifies the sterilization procedure required for a dialysis solution.

A still further advantage of the present invention is to provide a system, a package and a method that eliminates sticking in the bags, particularly the drain bag, in which solution is not normally provided.

Moreover, an advantage of the present invention is to provide a system, a package and a method that increases heat penetration and reduces overall time required for sterilization.

Another advantage of the present invention is to provide a system, a package and a method that eliminates excess air in the overpouch.

Another advantage of the present invention is to provide a system, a package and a method that eliminates excess volume required in the overpouch.

Yet another advantage of the present invention is to provide a system, a package and a method that uses a smaller overpouch.

Still further, an advantage of the present invention is to provide a system, a package and a method that reduces cost of packaging.

And, another advantage of the present invention is to provide a system, a package and a method that requires a smaller shipping carton for shipping the same number of packaged units thereby requiring less storage space at a home or location of the user or patient.

Moreover, an advantage of the present invention is to provide a system, a package and a method wherein each bag experiences less stress during sterilization.

Yet another advantage of the present invention is to provide a system, a package and a method that eliminates the requirement for bag orientation during sterilization.

A still further advantage of the present invention is to provide a system, a package and a method that allows separate storage of different solutions prior to mixing and subsequent administration to a patient.

And, another advantage of the present invention is to provide a system, a package and a method that stores different solutions separately without use of a frangible.

Still further, an advantage of the present invention is to provide a system, a package and a method that stores two components and/or solutions that are not compatible during manufacturing and/or storage.

Moreover, an advantage of the present invention is to provide a system, a package and a method for producing a sterilized bicarbonate/dextrose solution for peritoneal dialysis.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention relates to a system for conducting peritoneal dialysis. More specifically, the present invention relates to a system and a method for which peritoneal dialysis may be performed in a simplified manner.

Figure 1:
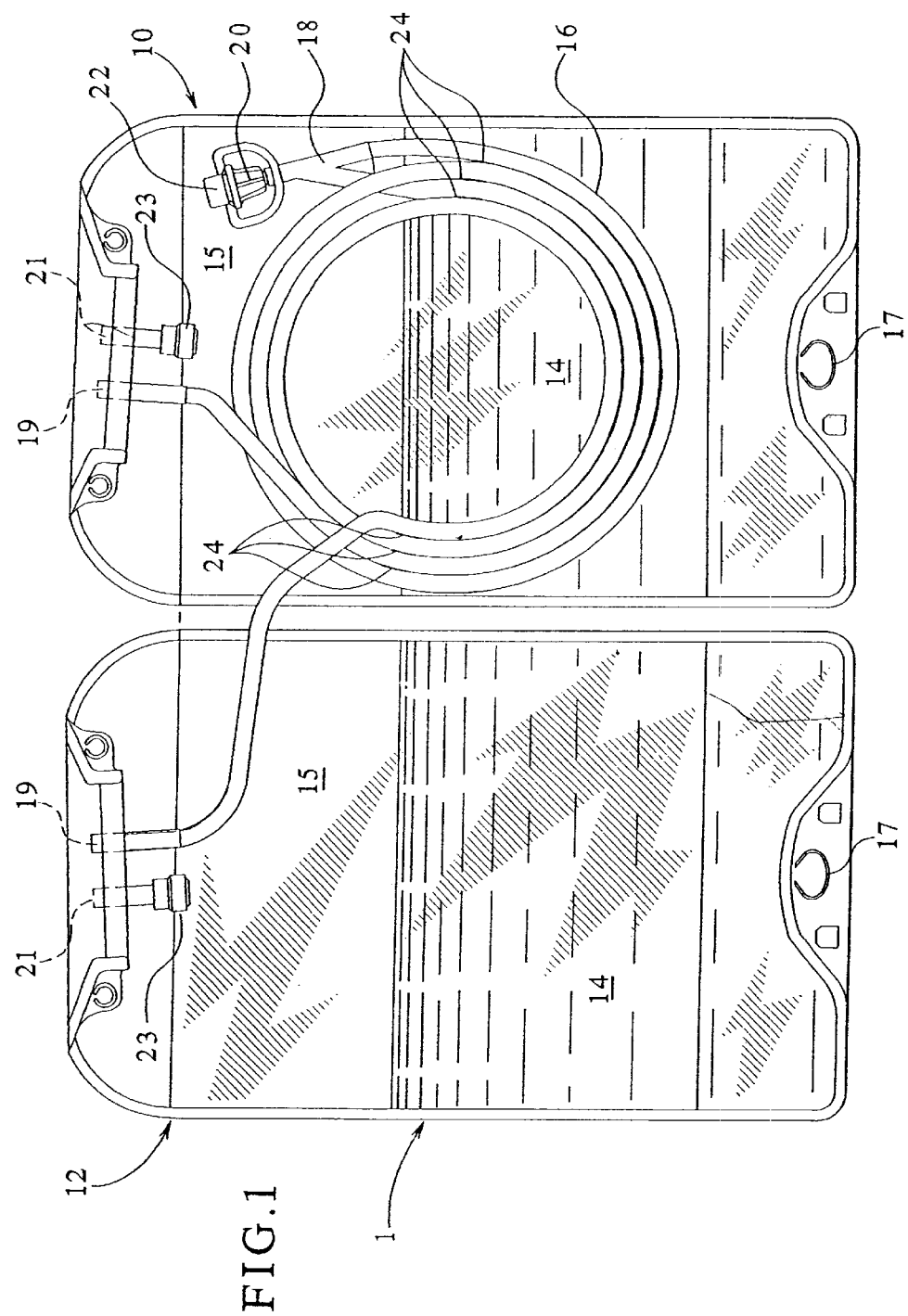
FIG. 1 illustrates a plan view of an embodiment of a dual-filled twin bag system of the present invention.

Referring now to the drawings wherein like numerals refer to like parts, FIG. 1 illustrates a dual-filled twin bag system 1 of the present invention wherein each bag, a solution bag 10 and a drain bag 12, is at least partially filled with a dialysis solution 14 within an interior of each of the bags 10,12. The bags 10,12 include apertures 17 from which the bags 10,12 can be suspended as required during a peritoneal dialysis procedure. During the manufacturing process of the system 1, the solution 14 is, preferably, equally filled and distributed in both the solution bag 10 and the drain bag 12.

In a typical situation, prior to the present invention, a drain bag is provided without solution therein. However, in accordance with the principles of the present invention, both the solution bag 10 and the drain bag 12 are at least partially filled with solution and preferably filled in substantially equal amounts. As a result, walls (see FIG. 3) of each of the bags 10,12 do not stick internally. That is, the solution 14 is held in the interior of the bags 10,12 between the exterior walls 18 of each of the bags 10,12 such that contact between the walls 18 is substantially eliminated, thereby eliminating sticking between the walls.

Connecting the bags 10,12 is a tubing set 16. The tubing set 16 includes ends connected to ports 19 of each of the bags 10,12. The ports 19 provide fluid communication between an interior of the bags 10,12 and the tubing of the tubing set 16. A second port 21 may also be provided on each or one of the bags 10,12. The second ports 21 have a cap 23 providing selective access to the interior of the bags 10,12. For example, it is often necessary to sample a fluid within the bags 10,12 during or after a dialysis procedure. The fluid may then be drawn from the second port 21 by a method known in the art.

During the manufacturing process, the tubing set 16 is connected to both of the bags 10,12. Then, in a preferred embodiment, the bags 10,12 via the tubing set 16 are filled with solution. A Y-connector 18 joins respective ends of the tubing set 16 providing fluid communication with each of the bags 10,12. A connector 20 terminates an end of the Y-connector 18. In turn, the connector 20, is enclosed by a cap 22, preferably a steam-permeable cap.

As illustrated, the tubing set 16 is in a coiled shape. The coiled shape is maintained by fusing or otherwise adhering the tubing set 16 at two junctions as designated by the slightly thicker lines 24 in FIG. 1. In addition to filling the bags 10,12 and the tubing set 16 during manufacture, the connector assembly, including the tubing set 16, the Y-connector 18 and the connector 20, may also be filled. Further, the Y-connector 18, in a preferred embodiment, is constructed substantially identically symmetrical. As a result, during filling of the solution bags 10,12 and the tubing set 16, which takes place during manufacture, through the Y-connector 18, a substantially equal volume of solution is fed into each of the bags 10,12.

Figure 2:
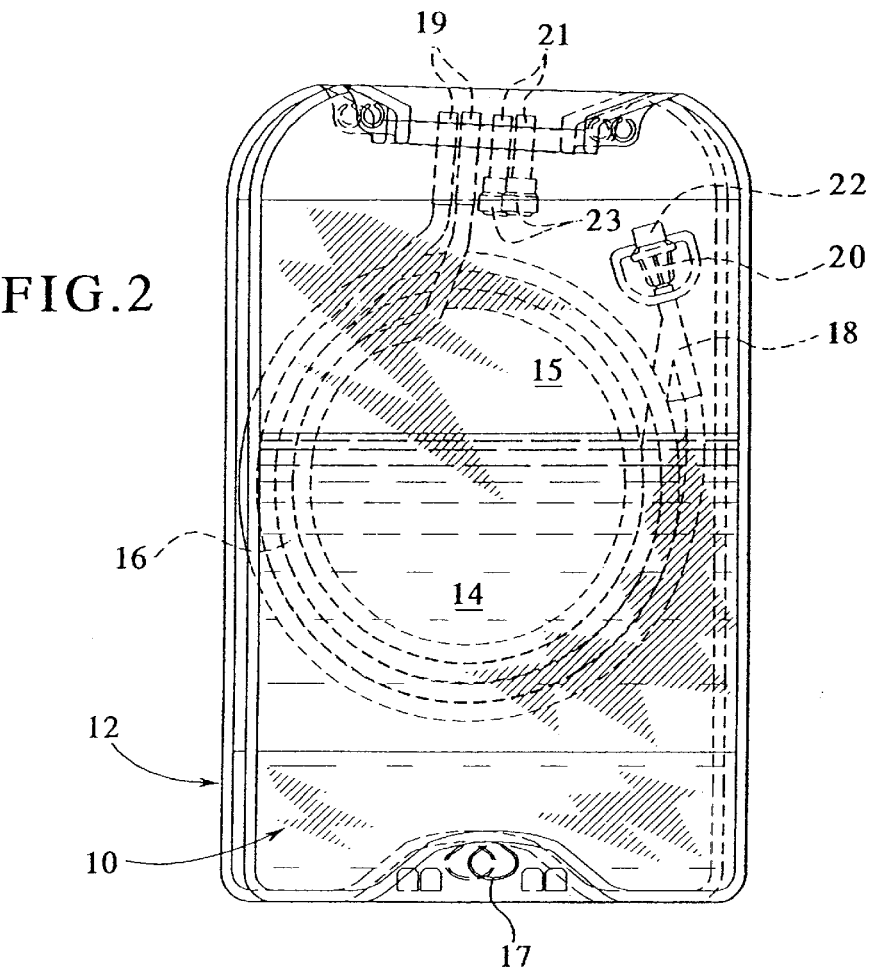
FIG. 2 illustrates a plan view of an embodiment of the dual-filled twin bag system of the present invention with one bag stacked atop another bag.
Figure 3:
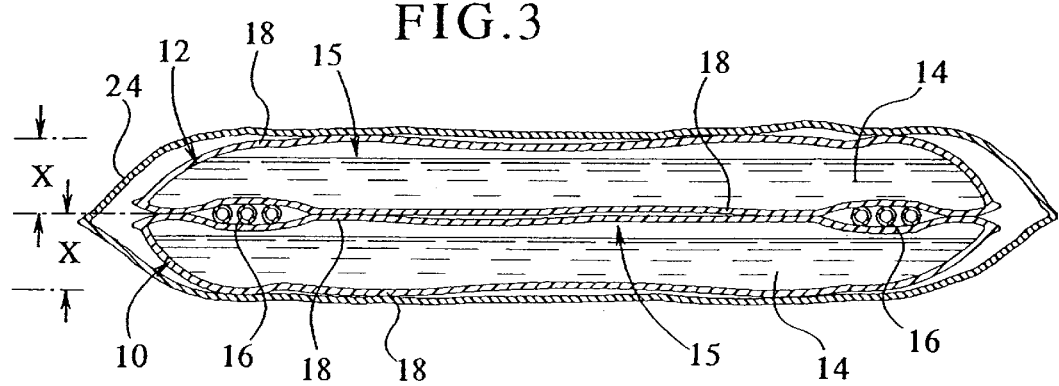
FIG. 3 illustrates a cross-sectional view of an embodiment of the dual-filled twin bag system of the present invention with one bag stacked atop the other bag with a coiled tubing set sandwiched between the bags within an overpouch.

Referring to FIGS. 2 and 3, as illustrated, the bags 10 and 12 are designed such that the coiled tubing set 16 is sandwiched between both of the bags 10,12 when filled with the solution 14. The sandwiched tubing set 16 situated between the bags 10,12 eliminates excess area typically required in an overpouch 24 in which the bags 10,12 and the tubing set 16 are transported. As a result, a smaller overpouch 24 than used in conventional twin bag systems may be implemented. Additionally, automatic overpouching is also simplified since the tubing set 16 is not encountered during the overpouching procedure, but merely the bags 10,12 themselves. That is, the bags 10,12 prevent interference of the tubing set 16 with the overpouch 24 during the overpouching procedure.

Still further, a smaller shipping carton (not shown) may also be implemented due to the reduced profile created using the bags 10,12 with the sandwiched tubing set 16. The bags 10,12 are also packed horizontally in the shipping carton thereby substantially reducing the size of the shipping carton. Horizontal placement of the bags 10,12 allows the solution to be distributed throughout the bags 10,12 rather than concentrated at the bottom of the bag during vertical positioning of the bag during shipment. As a result, lower cost per product may be achieved as well as lower shipping costs since more cartons may be incorporated in each pallet. In addition, less product storage space is required for a customer, such as a peritoneal dialysis patient, and less trash is discarded.

In addition, since each of the bags 10,12 includes a volume of the solution 14 therein, a larger footprint is created on a sterilizer tray during sterilization of the solution 14 in the bags 10,12. A larger footprint increases heat penetration and reduces overall time required for sterilization. Further, since, in a preferred embodiment, solution is contained in the tubing set 16, sterilization is more effectively and more quickly achieved. Further, lower exposure to heat may also improve color of the solution and allow for a higher pH solution to be implemented.

As shown in FIG. 3, with solution 14 in each of the bags 10,12, the profile of each of the bags 10,12 creates a height generally designated by X that is substantially less than a profile of a bag completely filled with solution necessary for administration to a patient during a dialysis procedure. In addition, because both of the bags 10,12 are at least partially filled and the coiled tubing set 16 is placed therebetween, orientation of the bags 10,12 during sterilization is not necessary. In addition, each of the bags 10,12 has less stress during sterilization since both of the bags 10,12 are filled with the solution 14.

In addition to the foregoing, due to the configuration of the system 1, the use of frangible assemblies is eliminated. That is, with both of the bags 10,12 at least partially filled with the solution 14, the necessity for maintaining separated areas in which solution does not flow until a frangible has been broken, has been eliminated. As a result, patients are not required to break a frangible, and particulate matter from breaking of the frangible which is often generated and forced into the fluid path during a dialysis procedure is eliminated. In addition, fibrin clotting is reduced.

In a preferred embodiment, the bags and tubing of the tubing set of the present invention are manufactured of a polyvinyl chloride (PVC) material. Alternatively, the bags and tubing may be manufactured of an ultra low density polyethylene. However, the bags 10,12 may also be manufactured of other non-polyvinyl chloride (PVC) materials, such as those materials taught and described in commonly assigned, co-pending U.S. patent application Ser. Nos. 08/153,602 and 08/153,823, both of which were filed on Nov. 16, 1993, the disclosures of which are incorporated herein in their entireties.

Although the illustrated bags are rectangular in shape, it should be understood that the bags could also be any other shape.

To use the dual-filled twin bag system of the present invention to administer solution to a patient, following sterilization, one of the bags 10 or 12 is suspended such that solutions can be drained from one of the bags 10 or 12 to the other bag. After solution is drained, the tubing of the tubing set 16 leading into the solution or full bag 10 is clamped to prevent egress of fluid therefrom.

Then, during a peritoneal dialysis procedure, the peritoneum of a patient may be drained into the empty bag 12. After draining, the solution 14 in the solution bag 10 may be infused into the patient. This may be accomplished by clamping the tubing leading to the bag containing the drain fluid and subsequently unclamping the tubing leading to the solution bag 10. Using the system of the present invention, draining time from the patient is substantially easier and faster since the drain bag 12 has been "pre-stressed" by already containing solution. Therefore, draining into the drain bag 12 is simplified with less resistance. Furthermore, the method of administering the solution including draining the peritoneum and infusing solution therein is performed without the use of any frangibles. Patients who are physically or visually impaired, therefore, overcome complications associated with a conventional twin bag system for a dialysis procedure.

Clamps for clamping the tubing leading to bags 10,12 may be of conventional design.

Preferably, the bags 10,12 are two liter or larger bags constructed from polyvinyl chloride (PVC) material and/or non-PVC material. A preferred non-PVC material is a multilayer film. The first layer is made of polypropylene (Amoco PP 8411). The second layer is a blend of ultra low density polyethylene (40% Mitsui Tafmer TF B01), polypropylene-ethylene copolymer (45% Solvay Fortilene 4265), and styrene-ethylene-butylene-styrene copolymer (15% Shell Kraton 1657). The third layer is a blend of an ultra low density polyethylene (40% Mitsui Tafmer TF B01), polypropylene-ethylene-copolymer (40% Solvay Fortilene 4265), acid modified styrene-ethylene butylene-styrene copolymer (10% Shell 1924X), and fatty acid amide (10% Henkel MM TPX 16-159). The overpouch 24 is further preferably constructed as a two liter or larger bag using high-density polyethylene (HDPE) or a $CO_2$ barrier film.

It will also be appreciated by those skilled in the art that the present invention may be utilized as a substitute for multiple chamber containers for mixing and administering different peritoneal dialysis solutions. By providing a single frangible within the tubing set 16 or clamping one section of the tubing set 16 prior to filling the bags 10,12, the bag 10 may be filled with one solution and the bag 12 may be filled with another different solution during manufacture. This may be desirable where the combined solutions may be unstable during long term storage or subject to degradation during sterilization. Immediately prior to use by the patient, the aforementioned clamp may be released, or the single frangible broken, so that the two different solutions may be mixed in one of the bags 10,12.

Alternately, the present invention may be utilized as a substitute for multiple chamber containers for different incompatible peritoneal dialysis solutions without the use of a frangible, clamp, or similar physical obstruction. This may be accomplished by filling each of the bags 10,12 with different solutions. Such filling can be conveniently accomplished through ports 23. After filling each bag 10,12, it is ensured that the tubing set 16 is free of fluid but filled with air or another gas. Then, the tubing set 16 is positioned or sandwiched between the bags 10,12, and the entire assembly is put in an overpouch 24 as illustrated in FIGS. 2 and 3. By thus sandwiching the tubing set 16 and packaging the set 16 and the bags 10,12 in the overpouch 24, the two different solutions may be kept separated until just prior to use. At the time of use, the overpouch 24 may be opened and solution in one bag may be drained into and thus mixed with the solution in the other bag. Administration and use of the mixed resultant solution can proceed as previously described.

Exemplary solutions were tested as follows:

TABLE 1

| Sol'n | Vol. | Dextrose Hydrous | Sodium Bicarbonate | Sodium Lactate | NaCl | $MgCl_2.6H_2O$ | $CaCl_2.2H_2O$ | Target pH range |
|---|---|---|---|---|---|---|---|---|
| 1 | 1 L | 8.5% | 0.0 mEq/L | 0.0 mEq/L | 0.0 g/L | 0.1 g/L | 0.508 g/L | System 1&2: 4.0–5.0; System 3: approx. 2 |
| 2 | 1 L | 0.0% | 4.2 g/L or 50 mEq/L Bicarbonate | 3.36 g/L or 30 mEq/L Lactate | 10.76 g/L | 0.0 g/L | 0.0 g/L | System 1&2: 7.0–7.7; System 3: approx. 9 |
| Target Resultant Solution | 2 L | 4.25% | 2.1 g/L or 25 mEq/L Bicarbonate | 1.68 g/L or 15 mEq/L Lactate | 5.38 g/L | 0.05 g/L or 0.5 mEq/L Mg | 0.254 g/L or 3.5 mEq/L Ca | 7.0–7.8 |

Three different systems were produced as follows:

TABLE 2

| System No. | Container Material | Overpouch Material | Solution No. 1's Target pH Range | Solution No. 2's Target pH Range |
|---|---|---|---|---|
| 1 | Non PVC | $CO_2$ Barrier Film | 4.0–5.0 | 7.0–7.7 |
| 2 | PVC | $CO_2$ Barrier Film | 4.0–5.0 | 7.0–7.7 |
| 3 | Non PVC | HOPE | about 2.0 | about 9.0 |

In an exemplary test of the present invention, batches of solutions 1 and 2 (See Table 1 for descriptions) were mixed and pH was adjusted, if necessary, to the target ranges. When required, the pH was adjusted with HCl (Hydrochloric Acid), NaOH (Sodium Hydroxide) or $CO_2$ (g) (Carbon Dioxide gas). The pH adjustment with NaOH or HCL changed the electrolyte composition slightly from the target resultant solution (See Table 1). However, the amount of NaCl may be modified in the formula to compensate for these pH adjustors.

After mixing, approximately one liter of each of solutions 1 and 2 was filled into separate two liter bags. The bags, sets and overpouches were then assembled together. The overpouches were sealed. The bags were then steam sterilized using a cycle required for two liter bags. Some bags were assembled as set forth above, but were not steam sterilized. These bags were considered pre-sterilized bags.

The containers and resultant solutions were chemically tested. The results of those tests are as follows:

TABLE 3

Chemical Testing Results

| Sol'n # | Steam Sterilized (Yes/No) | System # | pH (Units) @ 25° C. | Color (MSU) | 5HMF (Abs @ 284 nm) | Dextrose (% Hydrous) | pCO$_2$ (mmHg) @ 37° C. | HCO$_3$ (mmol/L) @ 37° C. | ctCO$_2$ (mmol/L) @ 37° C. | pH (Units) @ 37° C. | Sodium (mEq/L) |
|---|---|---|---|---|---|---|---|---|---|---|---|
| 1 | YES | 1 | 4.08 | 7 | 0.105 | 8.42 | 36.8 | ND | ND | ND | 3.4 |
| 2 | YES | 1 | 7.70 | 3 | 0.002 | 0.05 | 44.2 | 43.3 | 44.7 | 7.607 | 256.9 |
| Resultant | YES | 1 | 7.50 | 6 | 0.054 | 4.20 | 41.0 | 23.7 | 25.0 | 7.380 | 143.3 |
| 1-Control | NO | 1 | 4.85 | 6 | 0.002 | 8.42 | 23.0 | ND | ND | ND | 2.9 |
| 2-Control | NO | 1 | 7.55 | 3 | 0.001 | 0.01 | 63.6 | 44.3 | 46.3 | 7.461 | 253.7 |
| Resultant | NO | 1 | 7.45 | 5 | 0.002 | 4.25 | 46.7 | 24.6 | 26.1 | 7.340 | 143.5 |
| 1 | YES | 2 | 4.05 | 6 | 0.073 | 8.46 | 40.4 | ND | ND | ND | 2.2 |
| 2 | YES | 2 | 7.70 | 3 | 0.002 | 0.09 | 42.2 | 40.2 | 41.5 | 7.597 | 257.7 |
| Resultant | YES | 2 | 7.46 | 7 | 0.039 | 4.25 | 43.6 | 23.6 | 24.9 | 7.351 | 132.1 |
| 1-Control | NO | 2 | 4.47 | 6 | 0.001 | 8.55 | 20.5 | ND | ND | ND | 2.6 |
| 2-Control | NO | 2 | 7.56 | 3 | 0.002 | 0.02 | 61.7 | 42.2 | 44.1 | 7.453 | 255.8 |
| Resultant | NO | 2 | 7.46 | 5 | 0.001 | 4.26 | 45.5 | 23.8 | 25.2 | 7.337 | 143.7 |
| 1 | YES | 3 | 1.95 | 6 | 0.096 | 8.25 | ND | ND | ND | ND | 3.3 |
| 2 | YES | 3 | 9.01 | 5 | 0.007 | 0.51 | ND | ND | ND | ND | 252.7 |
| Resultant | YES | 3 | 7.42 | 6 | 0.053 | 4.12 | 47.7 | 25.0 | 26.4 | 7.337 | 149.7 |
| 1 | YES | 3 | 1.95 | 8 | 0.153 | 8.21 | ND | ND | ND | ND | 2.6 |
| 2 | YES | 3 | 9.05 | 4 | 0.002 | 0.02 | ND | ND | ND | ND | 253.7 |
| Resultant | YES | 3 | 7.36 | 9 | 0.082 | 4.13 | 53.1 | 23.6 | 25.2 | 7.265 | 146.1 |
| 1-Control | NO | 3 | 1.94 | 6 | 0.002 | 8.40 | ND | ND | ND | ND | 1.1 |
| 2-Control | NO | 3 | 9.07 | 3 | 0.002 | 0.05 | ND | ND | ND | ND | 264.7 |
| Resultant | NO | 3 | 7.47 | 5 | 0.003 | 4.09 | 45.3 | 25.2 | 26.6 | 7.364 | 153.5 |

In table 3, the following abbreviations were used: ND=None detected; MSU=Manostat Unit; nm=nanometer; mmol/L=millimol/liter; mmHg=inches of mercury; mEq/L=milliequivalents/liter; ctCO$_2$=calculated total CO$_2$; and 5HMF=5-hydroxymethylfurfural.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A method for forming a package for use during a peritoneal dialysis procedure, the method comprising the steps of:

providing a first container defining an interior;

providing a second container defining an interior;

connecting the first container and the second container; and filling simultaneously and at least partially the interiors of the first container and the second container with a solution.

2. The method of claim 1 further comprising the step of:

providing a tubing set including a length of tubing to connect the first container and the second container.

3. The method of claim 2 further comprising the step of:

sandwiching the tubing set between an exterior wall of the first container and an exterior wall of the second container.

4. The method of claim 1 further comprising the steps of:

providing a third container defining an interior; and placing the first container and the second container in the interior of the third container.

5. The method of claim 1 wherein the first container and the second container include substantially equal amounts of the solution.

6. The method of claim 1 further comprising the step of:

providing a coiled length of tubing to connect the first container and the second container.

7. The method of claim 1 wherein the first container and the second container are constructed from flexible materials.

8. The method of claim 1 wherein the solution in the first container is a different solution from the solution in the second container.

9. A method for forming a product for a peritoneal dialysis procedure, the method comprising the steps of:

providing a first container defining an interior;

providing a second container defining an interior;

filling, at least partially, the interiors of the first container and the second container with a solution; and sterilizing the containers.

* * * * *